US 7,459,128 B2
Dec. 2, 2008

(12) United States Patent
Karg et al.

(54) MICROFLUIDIC MIXING AND DISPENSING

(75) Inventors: Jeffrey A. Karg, Hopkinton, MA (US); Douglas W. Kroncke, Boston, MA (US)

(73) Assignee: Molecular BioProducts, Inc., San Diego, CA (US)

( * ) Notice: Subject to any disclaimer, the term of this patent is extended or adjusted under 35 U.S.C. 154(b) by 723 days.

(21) Appl. No.: 10/778,776

(22) Filed: Feb. 13, 2004

(65) Prior Publication Data
US 2004/0208794 A1 Oct. 21, 2004

Related U.S. Application Data

(63) Continuation of application No. PCT/US02/25653, filed on Aug. 13, 2002.

(51) Int. Cl.
*B01L 3/02* (2006.01)
(52) U.S. Cl. .................. 422/100; 422/99; 222/133; 73/864.13; 436/180
(58) Field of Classification Search ........... 422/99–101; 436/180; 73/864.72, 864.13; 222/133
See application file for complete search history.

(56) References Cited

U.S. PATENT DOCUMENTS

| 2,046,873 A | 7/1936 | Garrison |
| 2,260,888 A | 10/1941 | Davis |
| 2,427,606 A | 9/1947 | Johnson |
| 2,667,075 A | 1/1954 | Blum et al. |
| 2,902,155 A | 9/1959 | Lundeen |
| 3,365,064 A | 1/1968 | Horan, Jr. |
| 3,649,218 A | 3/1972 | Pontigny |
| 4,180,239 A | 12/1979 | Valukis |
| 4,268,481 A | 5/1981 | Suovaniemi et al. |
| 4,408,968 A | 10/1983 | Inagaki et al. |
| 4,451,220 A | 5/1984 | Ito et al. |
| 4,454,760 A | 6/1984 | Carlisle |
| 4,564,451 A | 1/1986 | Cohen |
| 4,844,868 A | 7/1989 | Rokugawa |

(Continued)

FOREIGN PATENT DOCUMENTS

DE 3115568 4/1982

(Continued)

*Primary Examiner*—Jill Warden
*Assistant Examiner*—Jyoti Nagpaul
(74) *Attorney, Agent, or Firm*—Fish & Richardson P.C.

(57) ABSTRACT

A microfluidic dispensing tap, such as for use in screening assays, includes a dispensing tube translatable within a sealed reservoir housing. The tube has an outer surface and defines an inner cavity open at a lower end of the tube, and a metering aperture extending through a side wall of the tube between the inner cavity and the outer surface to define a known volume. The tube is movable against a seal at a lower end of the reservoir housing between a first position, in which the metering aperture is disposed below the seal, and a second position, in which the metering aperture is disposed above the seal and exposed to the reservoir for entraining a discrete dose of a sample liquid within the aperture. An injector is configured to inject a known quantity of a diluent into the inner cavity of the tube and into fluidic contact with the dose of sample liquid in the aperture, such that the dose of sample liquid diffuses into the diluent to form a discrete mixture for dispensing from an open end of the tube.

16 Claims, 18 Drawing Sheets

U.S. PATENT DOCUMENTS

| | | |
|---|---|---|
| 5,074,154 A | 12/1991 | Allen et al. |
| 5,084,241 A | 1/1992 | Parker |
| 5,226,462 A | 7/1993 | Carl |
| 5,260,030 A | 11/1993 | DeVaughn |
| 5,454,268 A | 10/1995 | Kim |
| 5,558,509 A | 9/1996 | Jirnov et al. |
| 5,741,554 A | 4/1998 | Tisone |
| 5,743,960 A | 4/1998 | Tisone |
| 5,756,050 A | 5/1998 | Ershow et al. |
| 5,773,305 A | 6/1998 | Zabetakis et al. |
| 5,876,675 A | 3/1999 | Kennedy |
| 5,906,751 A | 5/1999 | Parker |
| 5,957,149 A | 9/1999 | Karg |
| 5,962,329 A | 10/1999 | Ershov et al. |
| 5,976,470 A | 11/1999 | Maiefski et al. |
| 6,024,925 A | 2/2000 | Little et al. |
| 6,085,773 A | 7/2000 | Karg et al. |
| 6,116,297 A * | 9/2000 | Feygin .................. 141/31 |
| 6,165,417 A | 12/2000 | Swierkowski |
| 6,416,718 B1 | 7/2002 | Maiefski et al. |
| 6,706,538 B1 | 3/2004 | Karg et al. |
| 2002/0187560 A1 | 12/2002 | Pezzuto et al. |
| 2003/0198576 A1 | 10/2003 | Coyne et al. |
| 2003/0210607 A1 | 11/2003 | Gilbert et al. |
| 2004/0028566 A1 | 2/2004 | Ko et al. |
| 2004/0072367 A1 | 4/2004 | Ding et al. |

FOREIGN PATENT DOCUMENTS

| | | |
|---|---|---|
| EP | 0971235 | 1/2000 |
| GB | 262126 | 8/1927 |
| GB | 392999 | 6/1933 |
| WO | WO9008075 | 7/1990 |
| WO | WO9804358 | 2/1998 |
| WO | WO9915876 | 4/1999 |
| WO | WO9943432 | 9/1999 |
| WO | WO9961881 | 12/1999 |
| WO | WO0024511 | 5/2000 |
| WO | WO0164345 | 9/2001 |
| WO | WO03016832 | 2/2003 |

* cited by examiner

MICROFLUIDIC MIXING AND DISPENSING

RELATED APPLICATIONS

This application is a continuation of PCT Application No. PCT/US02/25653, filed Aug. 13, 2002 and designating the United States, the entire contents of which are hereby incorporated herein by reference.

TECHNICAL FIELD

This invention relates to liquid dispensing devices for mixing and dispensing extremely small quantities of liquids, and arrays of such devices for use in microfluidics and laboratory automation.

BACKGROUND

The science and economics of drug discovery has changed with developments in the areas of genomics, combinatorial chemistry and high-throughput screening. The number of targets has increased as a result of genomics while the number of small molecule compounds (samples) has dramatically increased as a result of combinatorial chemistry. This increase in targets and compounds has an exponential effect on the number of tests that need to be performed to increase the likelihood of finding a new chemical entity using high-throughput screening. Microliter amounts of target and sample must suffice for many screening assays, putting pressure on the automation industry to provide new tools to accurately meter, mix and dispense liquids in doses as low as on the order of 10 nanoliters in many instances. Conventional R&D screening efforts use multiple variations of pipetting to move aliquots of the concentrated liquid sample from storage receptacles, to working receptacles, to dilution receptacles where the sample is diluted with a solvent such as pure dimethylsulfoxide (DMSO), and finally to assay receptacles. This "reformatting" process, or "sample preparation" can waste valuable sample or target and increase time and assay cost. Devices and methods are needed for accurately and efficiently handling these valuable liquids in such minute quantities, to increase screening productivity and accuracy.

SUMMARY

The invention features a microfluidic dispensing tap configured to accurately meter and dilute extremely small amounts of liquids, such as sample fluids for screening assays.

According to one aspect of the invention, the tap has a dispensing tube having an outer surface and defining an inner cavity open at a lower end of the tube, the tube also defining a metering aperture extending through a side wall of the tube between the inner cavity and the outer surface, the metering aperture defining a known volume. The tap also includes a reservoir housing defining, together with the tube outer surface, a reservoir cavity for holding a quantity of a first liquid, and a seal between the reservoir housing and the tube outer surface at a lower end of the reservoir, the tube being movable against the seal between a first position, in which the metering aperture is disposed below the seal, and a second position, in which the metering aperture is disposed above the seal and exposed to the reservoir for entraining a discrete dose of the first liquid within the aperture. An injector is hydraulically connected to the inner cavity of the tube and configured to inject a known quantity of a second liquid into the inner cavity of the tube and into fluidic contact with the dose of first liquid in the aperture, such that the dose of first liquid diffuses into the quantity of second liquid to form a discrete mixture for dispensing from the open end of the tube, such as into a well.

Preferably the tap does not contact the well, and the liquid dispensed from each tap breaks contact with the tap before contacting the well aligned with that tap or the contents of the well aligned with that tap. The reservoirs are preferably sealed against air and light. The taps may be configured in an array of reservoir units aligned directly above an array of wells. Each tap may be actuated independently and preferably contains zero dead volume. Examples of suitable multi-well containers are a 96-well microtiter plate, a 384-well microtiter plate and a 1536-well microtiter plate.

In some embodiments, the aperture is a metering capillary and the first liquid is drawn via capillary forces into the metering capillary.

In some cases the tap includes means for cycling the solution up and down within the inner cavity of the tube, such as through a mixing orifice, to thoroughly mix the first and second liquids before dispensing. For example, the injector may be configured to perform such cycling pneumatically.

Some embodiments include means for propelling the mixed solution from the tube utilizing a compressed gas, such as air, nitrogen or argon, that engages an exposed surface of the solution. Alternatively, the fluid can be drawn from the end of the tube by touching the solution to another fluid surface or a solid surface.

The invention also features a device for storing and dispensing liquid into an array of wells in a multi-well container. The device includes: an array of isolated, sealed, tapped reservoir units, each unit containing an integrated metering tap, each tap including a meter capillary. The meter capillary can be sized to draw in, for example, 5 nanoliters to 20 microliters, preferably from 5 to 200 nanoliters of a liquid. The device also includes suitable instrumentation to pump a diluent in through the inner diameter of the tube so that the lower meniscus edge is below the meter capillary, drawing the liquid into the diluent via diffusion or forced vacuum, mixing the liquid and diluent in the tube by hydraulically moving the diluent up and down inside of the tube, and expelling the mixture from the tube by pumping the diluent to the end of the translatable tube. The array of reservoir units can be arranged so that each tap aligns with one well of a multi-well container such as a 96-well microtiter plate, a 384-well microtiter plate, a 1536-well microtiter plate or a flat plate designed to hold small amounts of fluid. However, with suitable equipment, any particular tap can be positioned to dispense into any chosen well. Some embodiments of the invention include a compressed gas inlet port in fluid communication with the fluid output path when the tube is in the dispense position. In addition, some embodiments include a compressed gas path terminating in an annular opening surrounding the fluid output tip. Some embodiments of the invention feature a single channel device that operates independently or operates as an array by placing multiple single-channel units into a frame.

According to another aspect of the invention, a microfluidic dispensing tap includes a dispensing tube having an outer surface and defining an inner cavity open at a lower end of the tube. The tube also defines a metering aperture extending through a side wall of the tube between the inner cavity and the outer surface, the metering aperture defining a known volume. A reservoir housing defines, together with the tube outer surface, a reservoir cavity for holding a quantity of a first liquid. A seal extends between the reservoir housing and the tube outer surface at a lower end of the reservoir cavity. The tube is movable against the seal between a first position, in which the metering aperture is disposed below the seal, and a second position, in which the metering aperture is disposed above the seal and exposed to the reservoir cavity for entraining a discrete dose of the first liquid within the aperture. A tap actuator is hydraulically connected to the inner cavity of the tube and configured to introduce a known quantity of a second liquid into the inner cavity of the tube and into fluidic contact with the dose of first liquid in the aperture, such that the dose of first liquid diffuses into the quantity of second liquid to form a discrete mixture for dispensing from the open end of the tube.

Preferably, the reservoir cavity is sealed against air and light.

In some embodiments, the aperture is a metering capillary and the first liquid is drawn via capillary forces into the metering capillary.

The actuator is preferably adapted to cycle the solution up and down within the inner cavity of the tube to mix the first and second liquids before dispensing, such as by cycling through a mixing orifice. The mixing orifice may be defined at (i.e., aligned with) a detent in the outer surface of the tube, for example. The tap actuator may be configured to perform such cycling pneumatically.

In some cases, the tap also includes means for propelling the mixed solution from the tube utilizing a compressed gas, such as air, nitrogen or argon, that engages an exposed surface of the solution. For example, a compressed gas inlet port may be provided in fluid communication with the inner cavity of the tube when the tube is in a dispense position, or a compressed gas path may terminate in an annular opening surrounding the lower end of the tube.

In some embodiments, the second liquid is introduced into the inner cavity of the tube by injecting the second fluid into the tube at a point where the metering aperture is between the injected second fluid and said open end of the tube. In some other embodiments, the second liquid is introduced into the inner cavity of the tube by being drawn up from the open end of the tube toward the metering aperture.

The metering aperture or capillary preferably has a fixed volume of less than about 20 microliters, more preferably between about 5 and 200 nanoliters.

In some configurations, a multiplicity of the above-described dispensing taps are arranged in an array alignable with an array of wells of a microtiter plate, into each of which the mixed solution is expelled from a corresponding dispensing tap by operating the corresponding tap.

According to another aspect of the invention, a device is provided for storing and dispensing liquid into an array of wells in a multi-well container. The device includes an array of isolated, sealed, tapped reservoir units, each unit containing an integrated metering tap including a dispensing tube having an outer surface and defining an inner cavity open at a lower end of the tube. The tube also defines a metering capillary extending through a side wall of the tube between the inner cavity and the outer surface, the metering capillary sized to draw in a known volume of a liquid. The device includes instrumentation configured to pump a diluent along the inner cavity of the tube so that a lower meniscus edge of the diluent is below the metering capillary; draw the liquid from the metering capillary into the diluent via diffusion or forced vacuum; mix the liquid and diluent in the tube by hydraulically moving the diluent up and down inside the tube, to form a mixture; and then expel the mixture from the tube by pumping the mixture to the end of the tube.

In preferred embodiments, the array of reservoir units is arranged so that each tap aligns with one well of a multi-well container such as a 96-well microtiter plate, a 384-well microtiter plate, a 1536-well microtiter plate or a flat plate designed to hold small amounts of fluid.

According to another aspect of the invention, a method of mixing and dispensing microliter volumes of a sample liquid with a diluent liquid is provided. The method includes:
(a) providing a sealed, tapped reservoir unit containing an integrated metering tap with a dispensing tube having an outer surface and defining an inner cavity open at a lower end of the tube, the tube also defining a metering capillary extending through a side wall of the tube between the inner cavity and the outer surface;
(b) drawing a dose volume of sample liquid into the metering capillary by capillary action;
(c) pumping a volume of liquid diluent along the inner cavity of the tube so that a lower meniscus edge of the diluent is below the metering capillary;
(d) drawing the dose of sample liquid from the metering capillary into the diluent, such as by diffusion or forced vacuum;
(e) mixing the sample liquid and diluent in the tube to form a mixture; and then
(f) expelling the mixture from the tube by pumping the mixture to the end of the tube.

In some cases the volume of liquid diluent is introduced into the inner cavity of the tube by injecting the diluent into the tube at a point where the metering aperture is between the injected diluent and the end of the tube. In some other cases, the liquid diluent is introduced into the inner cavity of the tube by being drawn up from the end of the tube toward the metering aperture.

In some applications, mixing includes hydraulically moving the diluent up and down inside the tube, and may include cycling the sample liquid and diluent through a mixing orifice. The diluent may be moved up and down inside the tube pneumatically, for example.

In some embodiments, expelling the mixture from the tube includes engaging an exposed surface of the mixture with a compressed gas, such as air, nitrogen or argon.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1:
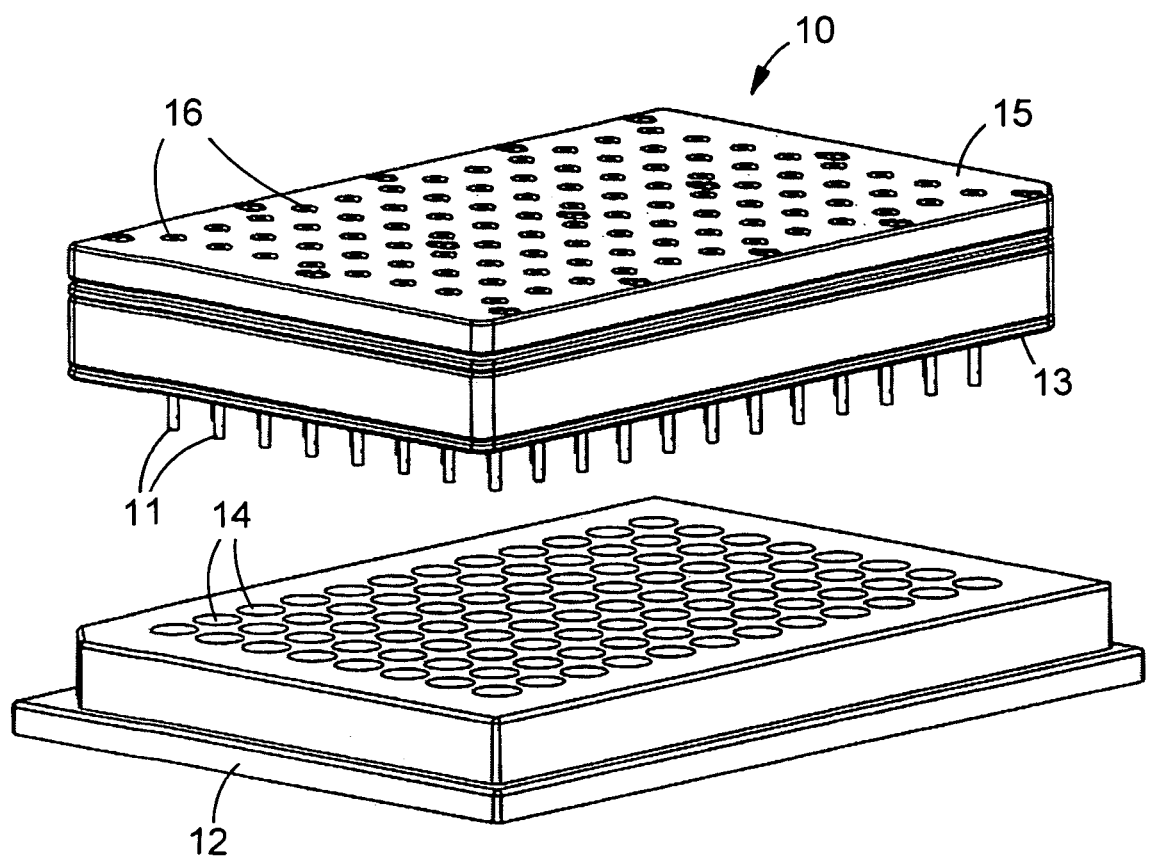
FIG. 1 is a perspective view of a device for integrated storage, integrated dilution and single-channel dispensing of small volumes of liquids, having multiple tap units.

Referring to FIG. 1, a microfluidic dispensing device 10 is useful for storing and dispensing liquid into a conventional 96-well microtiter plate 12. The depicted device contains a 96-unit array of integrated reservoir/tap units. The 96 units are arranged so that each of the 96 tubes aligns with one well of a conventional 96-well microtiter plate. Protruding from lower surface 13 of device 10 are 96, 384, 1536 or other configuration of flow tubes 11 arranged so that when device 10 is aligned above a 96, 384, 1536 microtiter plate or other receptacle 12, each flow tube 11 is above a different one of the 96, 384, 1536, or other number of wells or receptacles 14. On the upper surface 15 of device 10 are 96, 384, 1536, or other number of mechanical interfaces 16 for tap actuation. Operation of each interface 16 actuates a tap whose flow tube 11 is located beneath that interface 16. Alternatively, a mechanical interface can be provided on the lower end of each tube 11, with the flow path of tubes 11 reversed.

Figure 2:
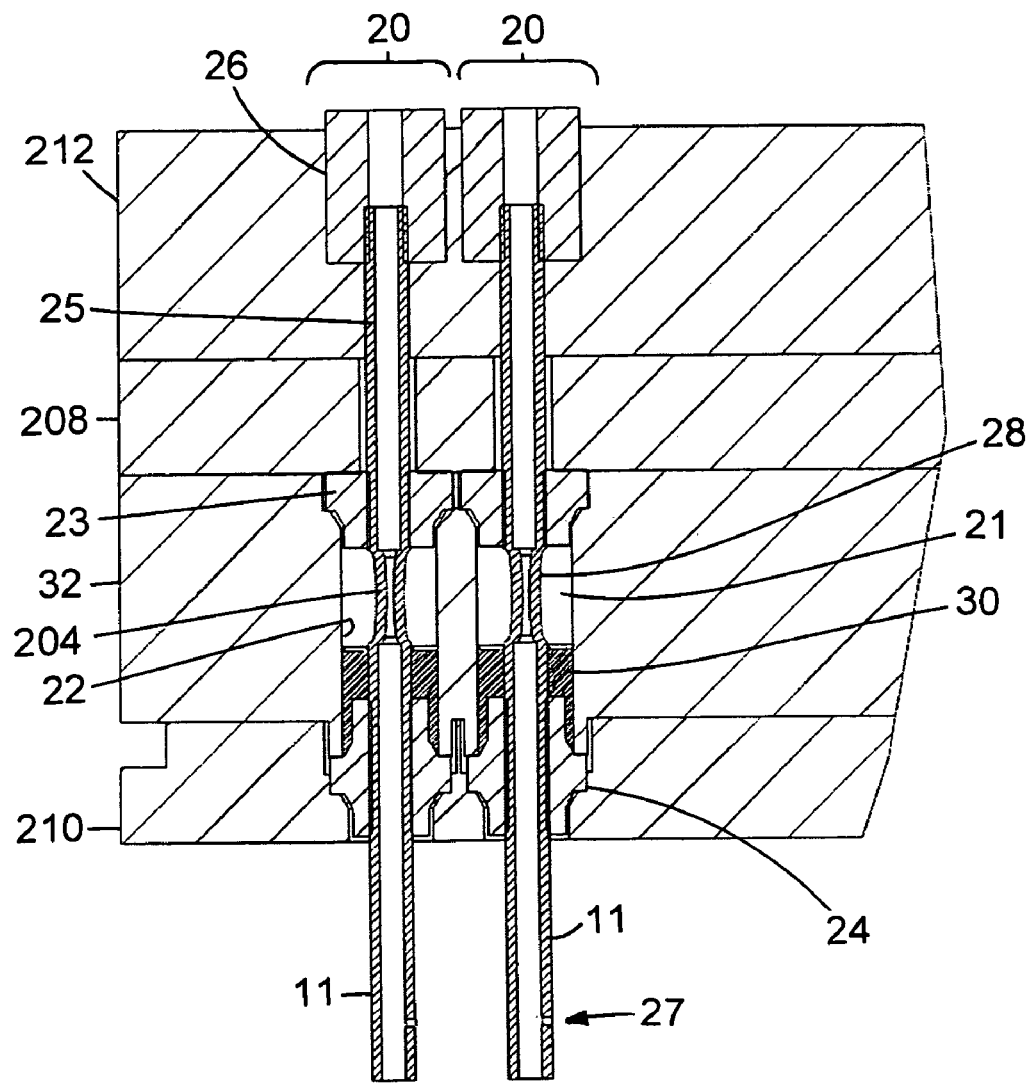
FIG. 2 shows a sectional view of two arrayed tap units, with metering tubes in a down position.
Figure 3:
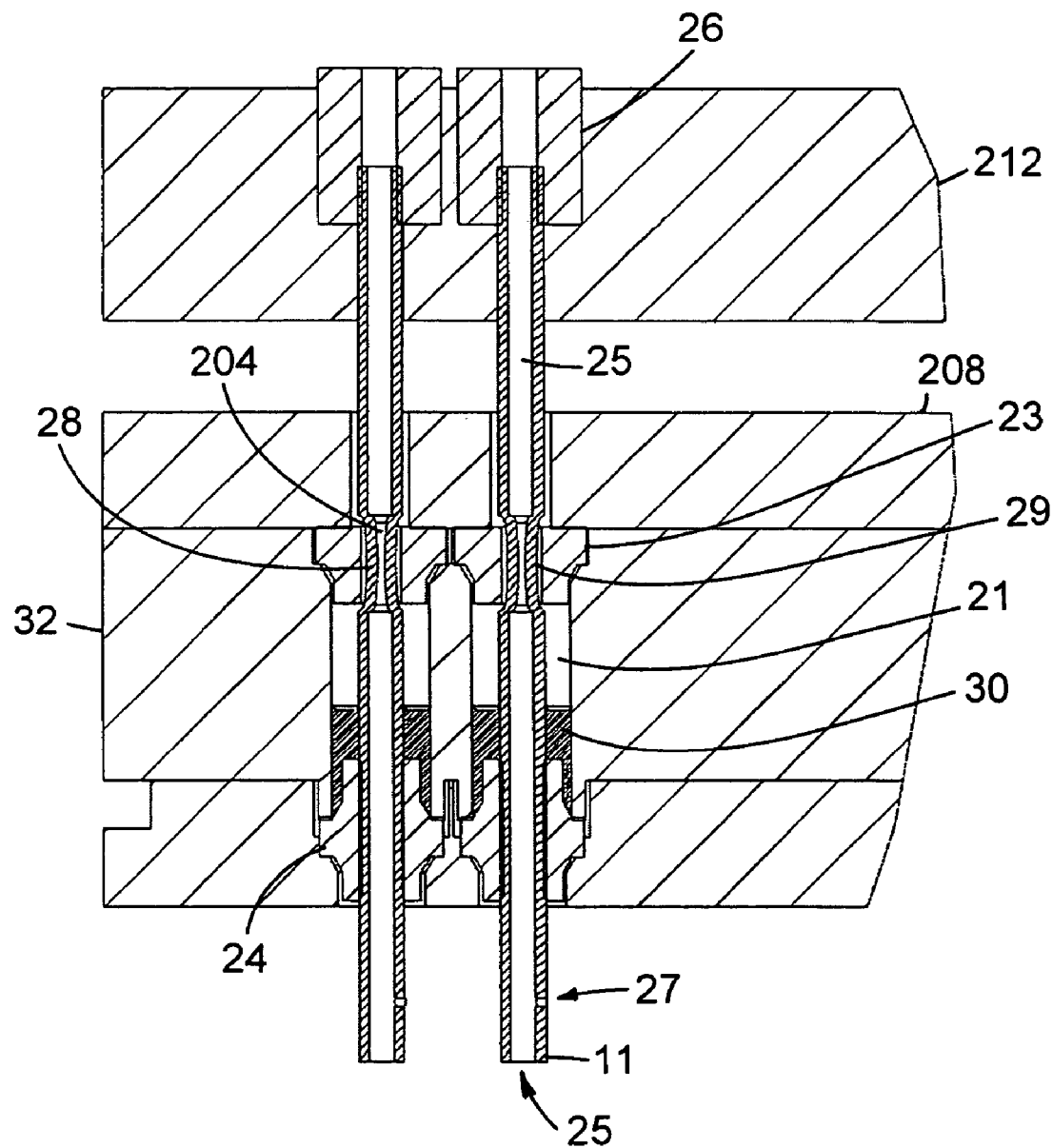
FIG. 3 shows the tap units with the metering tubes in an intermediate up position.

FIGS. 2 through 5 illustrate sample fluid metering. As shown in FIG. 2, each tap unit 20 contains a reservoir 21 around the outer diameter of its tube 11, defined by a cylinder wall 22 of reservoir plate 32 between upper and lower seals 23 and 24 providing dynamic sealing against the outer surface of the tube 11. Seals 23 and 24 may be of any suitable material compatible with the fluids to be contained in reservoirs 21. For use with DMSO as a solvent, molded silicone coated with polytetrafluoroethylene (PTFE) is a suitable seal material for providing a contacting seal surface against the outer surface of each tube 11. Non-coated silicone may be employed, but DMSO can pull impurities from silicone, resulting in possible sample contamination. The seals may be individual units held in place by upper and lower seal retaining plates 208 and 210 of polypropylene, as shown, or portions of a common sealing member spanning multiple reservoirs. Each reservoir 21 contains a quantity of sample fluid 30. Each round tube 11 is hollow, defining a central bore 25, and has a midsection detent 28 of reduced diameter, defining an inner mixing orifice 204. Tubes 11 have a nominal outer diameter of about 1.5 millimeters, and a nominal inner diameter of bore 25 of about 0.8 millimeter. A mechanical interface 26 is disposed at the upper end of each tube 11 and held within an interface plate 212, for hydraulically connecting the tube to an actuation instrumentation manifold block (not shown). Each meter/dilution/dispensing tube 11 also defines a meter capillary 27 hydraulically connecting the outside of the tube 11 with the inside bore 25 of the tube, below the mixing orifice 204. Capillaries 27 define fixed volumes within the thickness of the side wall of each tube. In the illustrated embodiment, tubes 11 are of polypropylene and capillaries 27 are round holes having a diameter of about 0.28 millimeter and a length (equal to the wall thickness of the tube) of about 0.34 millimeter, defining a capillary volume of approximately 15 nanoliters. The metered amount can be from near zero nanoliters to 20 microliters, preferably from 5 to 200 nanoliters. Mixing orifices 204 need not be at the same position along tubes 11 as necked detents 28.

Figure 4:
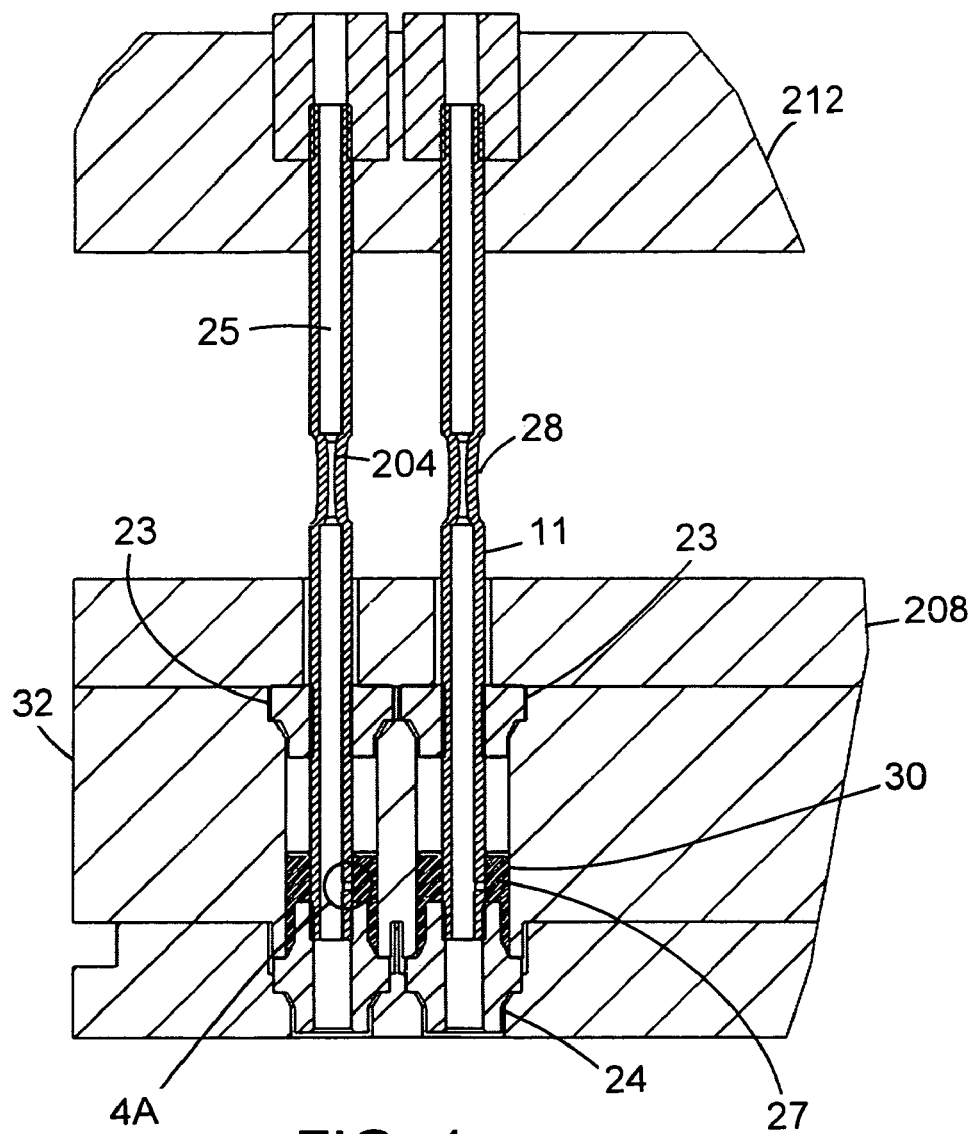
FIG. 4 shows the tap units with metering tubes in an up position.
Figure 4A:
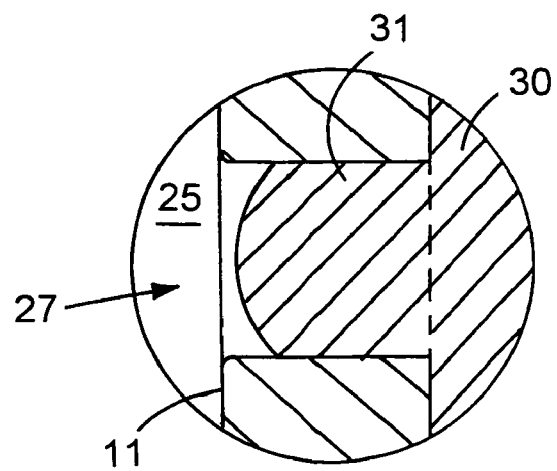
FIG. 4A is an enlarged view of section 4A of FIG. 4.

In operation, the metering tubes 11 are first translated up to an intermediary position (FIG. 3) by moving the interface plate 212 away from upper seal plate 208. In this position, tube detent 28 is aligned with, and fully spans, upper seal 23 to allow nitrogen or other inert gas to enter the reservoir 21 through open channel 29 defined between upper seal 23 and the outer surface of tube 11, to balance internal reservoir pressure. Detent 28 may be of any other form suitable for performing this pressure-balancing function, such as one or more longitudinal grooves extending a limited distance along the outer surface of the tube. Tubes 11 continue to be pulled upward to an up position (FIG. 4), where meter capillaries 27 are in direct exposure to stored sample fluid 30 in reservoirs 21. With reservoir pressure having just been established by the temporary spanning of detent 28 across upper seal 23, a determinable amount of fluid sample 30 will be drawn into each capillary 27 by capillary action, as a function of capillary volume and surface tension effects, forming a metered fluid dose 31 (FIG. 4A). Typically, the inner meniscus of metered dose 31 will not protrude into the inner tube bore 25. In the tube position shown in FIG. 4, reservoir 21 is now completely sealed from the outside by cylinder wall 22, upper seal 23 and lower seal 24.

Figure 4B:
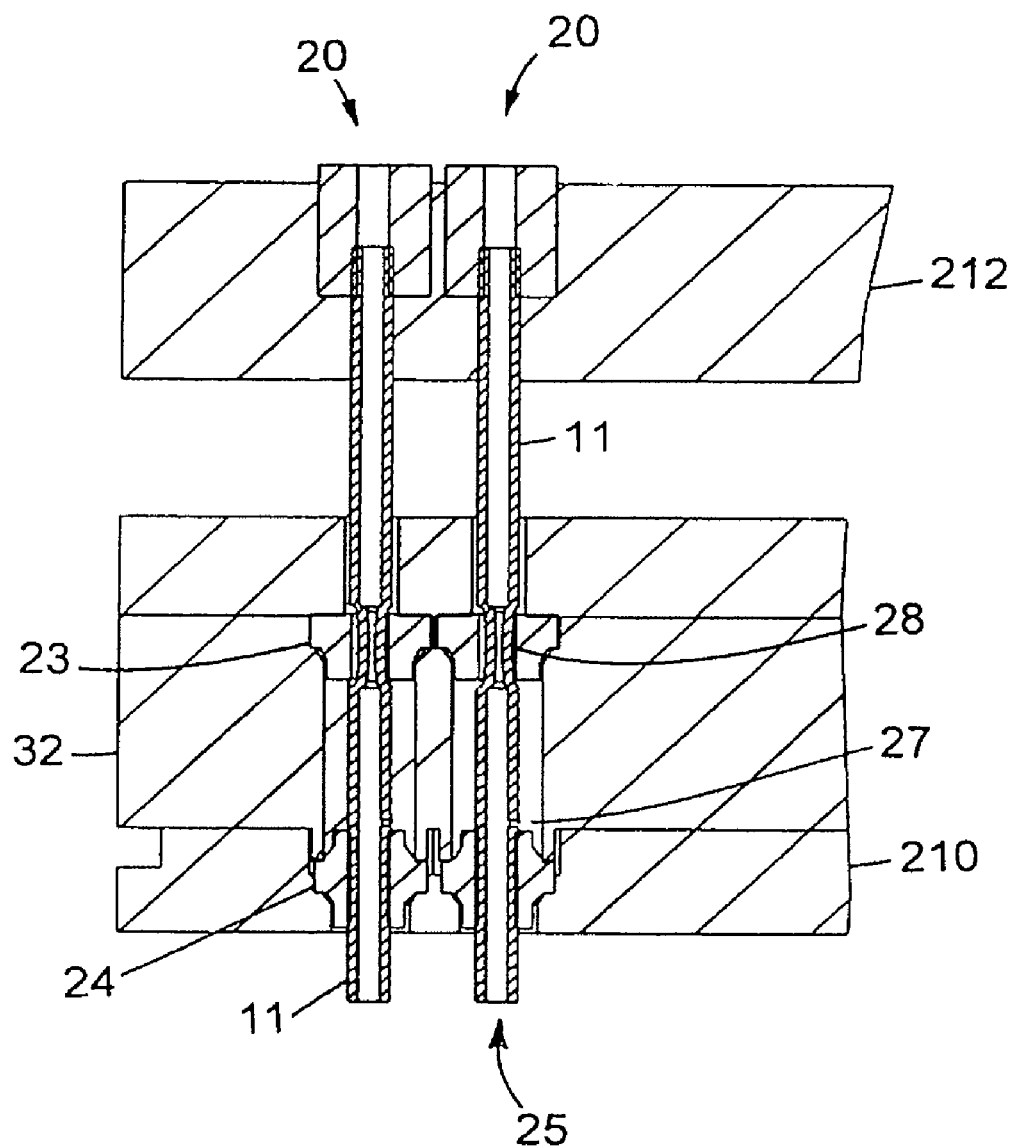
FIG. 4B illustrates metering during pressure equalization in a second embodiment.
Figure 5:
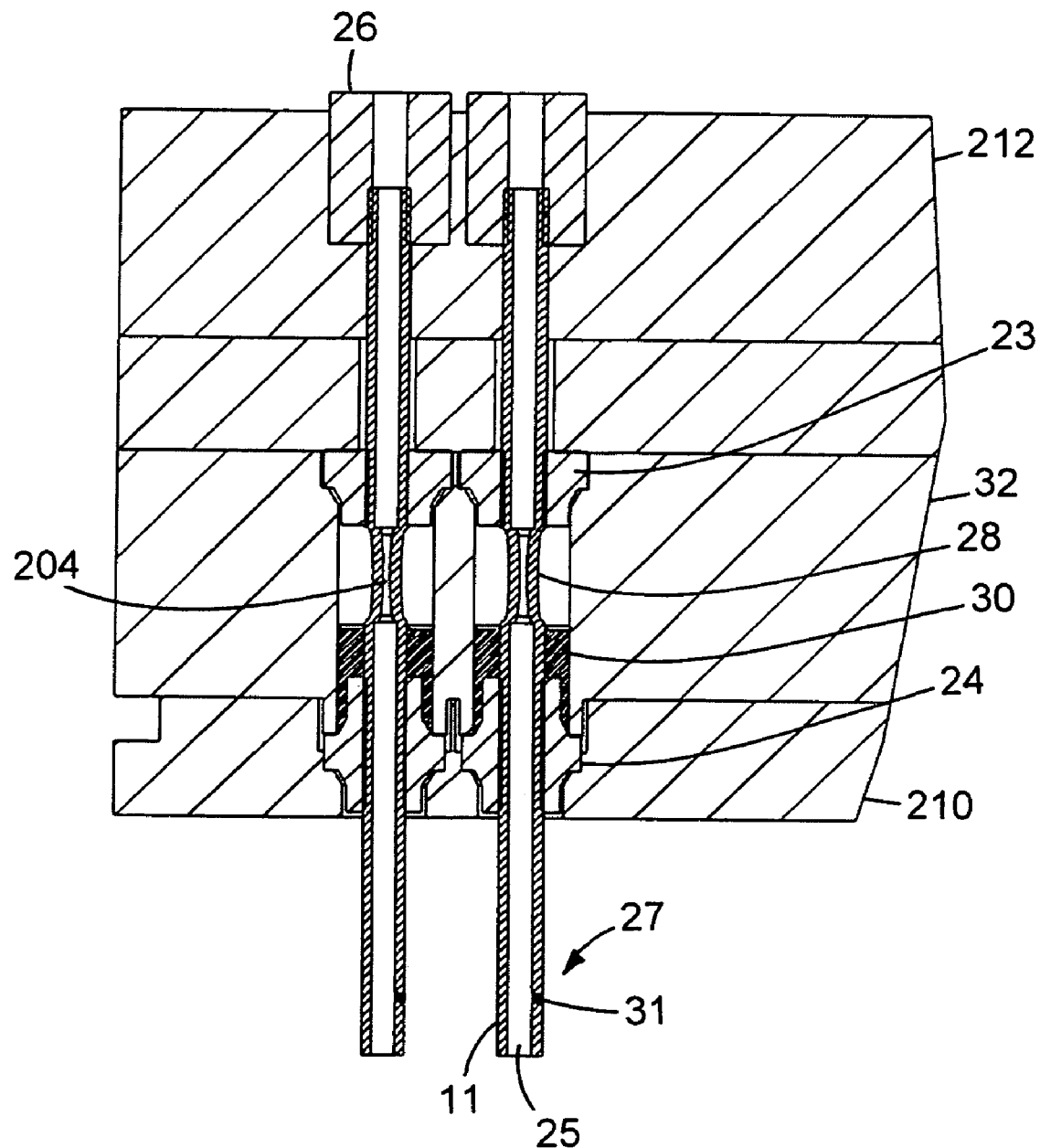
FIG. 5 shows the embodiment of FIG. 2 with metering tubes in a down position with filled capillaries for dispensing.

Alternately, reservoir pressure equalization may be timed to coincide with metering by repositioning detent 28 with respect to capillary 27, as shown in FIG. 4B. In the illustrated position of tube 11, tube detent 28 momentarily spans upper seal 23 to allow nitrogen or other inert gas to enter the reservoir 21 through channel 29 to balance the internal reservoir pressure, while capillary 27 is exposed to sample fluid in reservoir 21.

As the outside of the tube 11 (at the site of capillary 27) comes in contact with the fluid, capillary forces and the relationship between the surface tension of the fluid and the surface energy of the tube material will draw fluid into the capillary hole 27 until the volume of that capillary hole is substantially filled. A meniscus forms at the inside surface of the tube 11. A meniscus is often described in the form of a contact angle between the fluid and the material. The contact angle will vary according to the relationship between the surface tension of the fluid and the surface energy of the tube material. A variation in contact angle will cause the volume of the capillary to vary slightly. The surface tension (fluid) and surface energy (solid) relationship is optimized when the fluid has a low surface tension (e.g. 20-70 dynes per centimeter) and the solid has a relatively high surface energy (e.g. 30-100 dynes per centimeter).

The metering tubes 11 are next moved back to a down position (FIG. 5), with the meter capillaries 27 again beneath lower seals 24 and now containing known volumes 31 of sample fluid separated from the remaining fluid in reservoirs 21 by the wiping action of lower seals 24.

Figure 6:
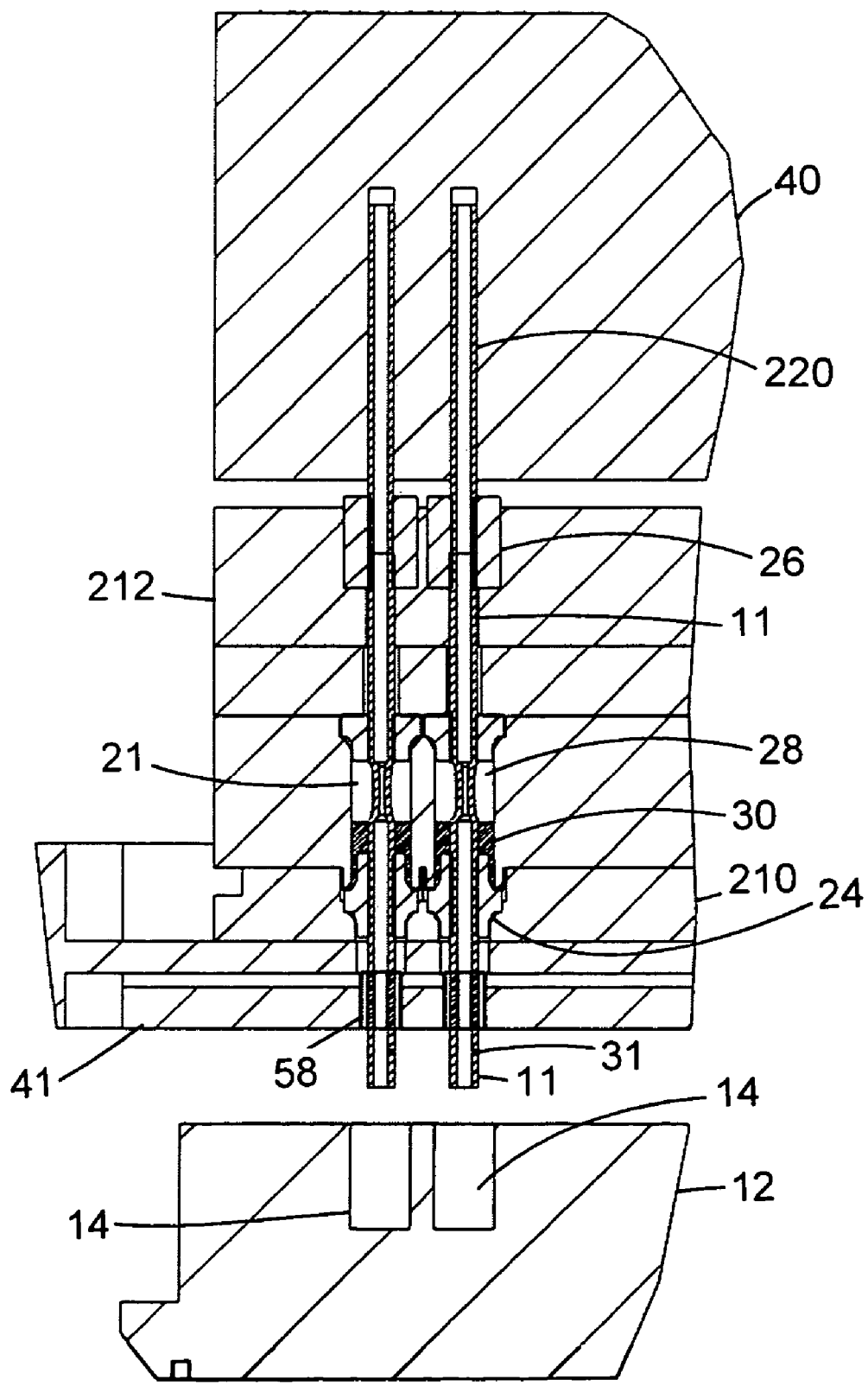
FIG. 6 shows the tap units combined with actuation instrumentation and an arrayed assay receptacle.
Figure 7:
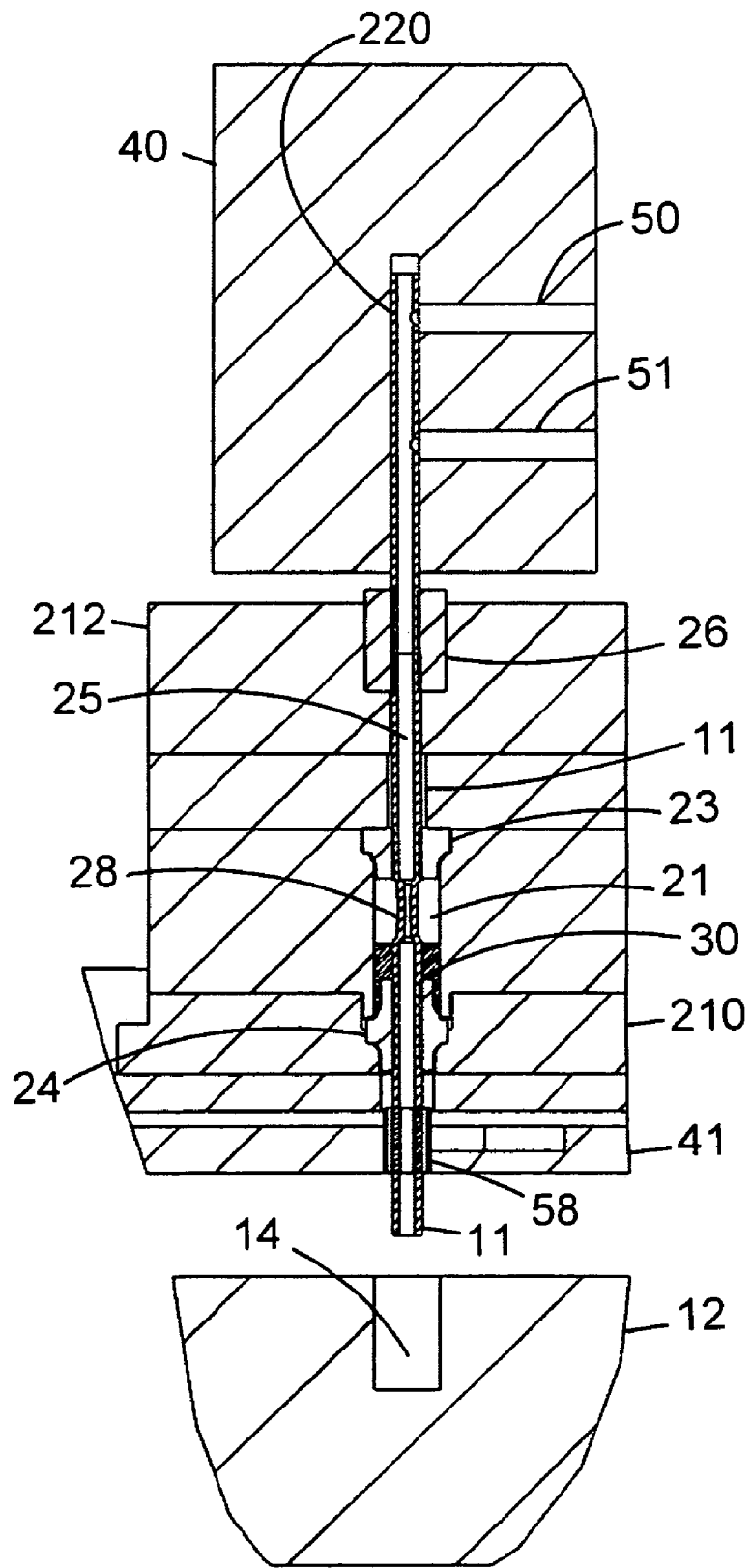
FIG. 7 shows one of the tap units as shown in FIG. 6, viewed from the right side.
Figure 8:
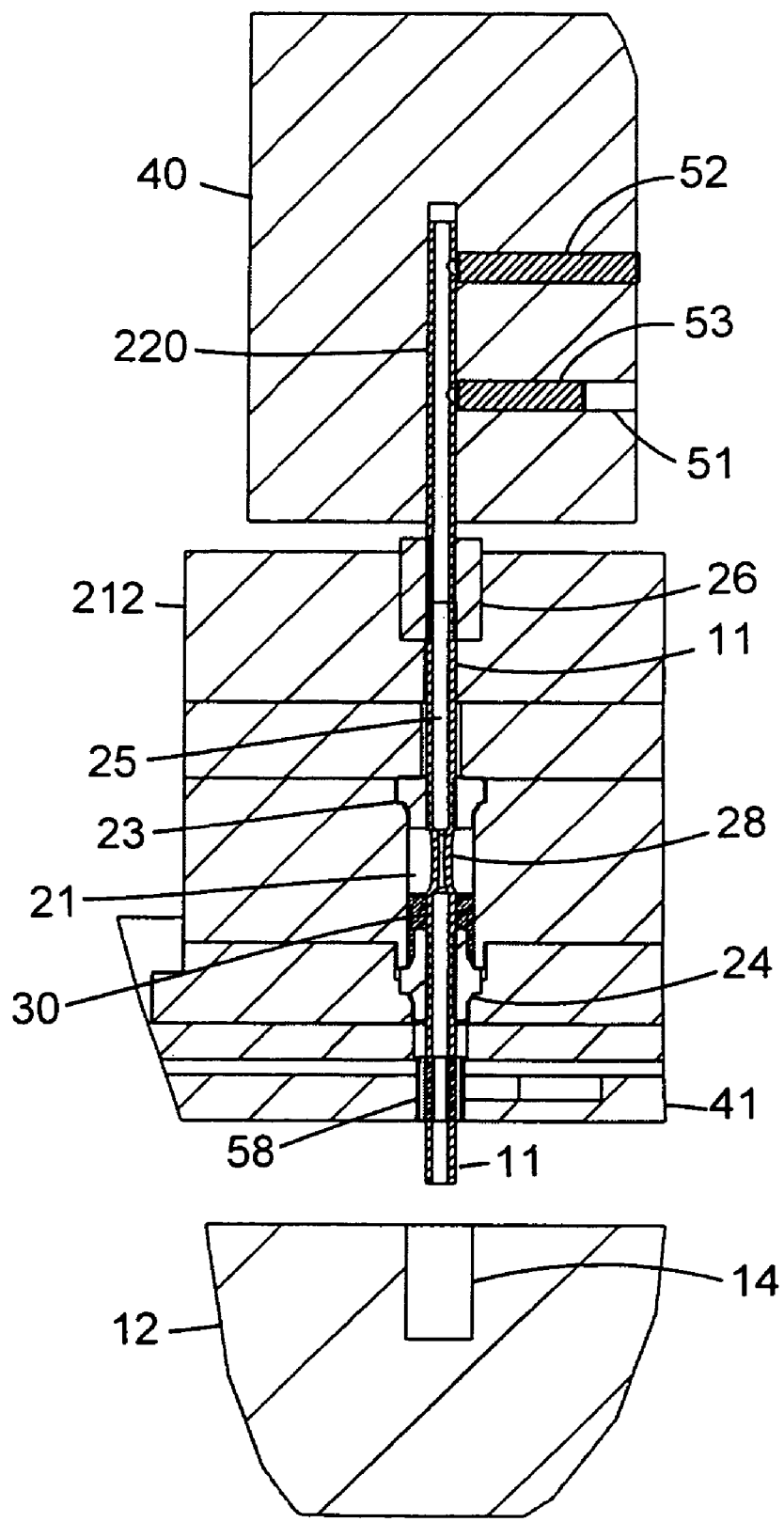
FIGS. 8-10 sequentially illustrate the positioning of a quantity of diluent in contact with the filled capillary, for diffusion.
Figure 9:
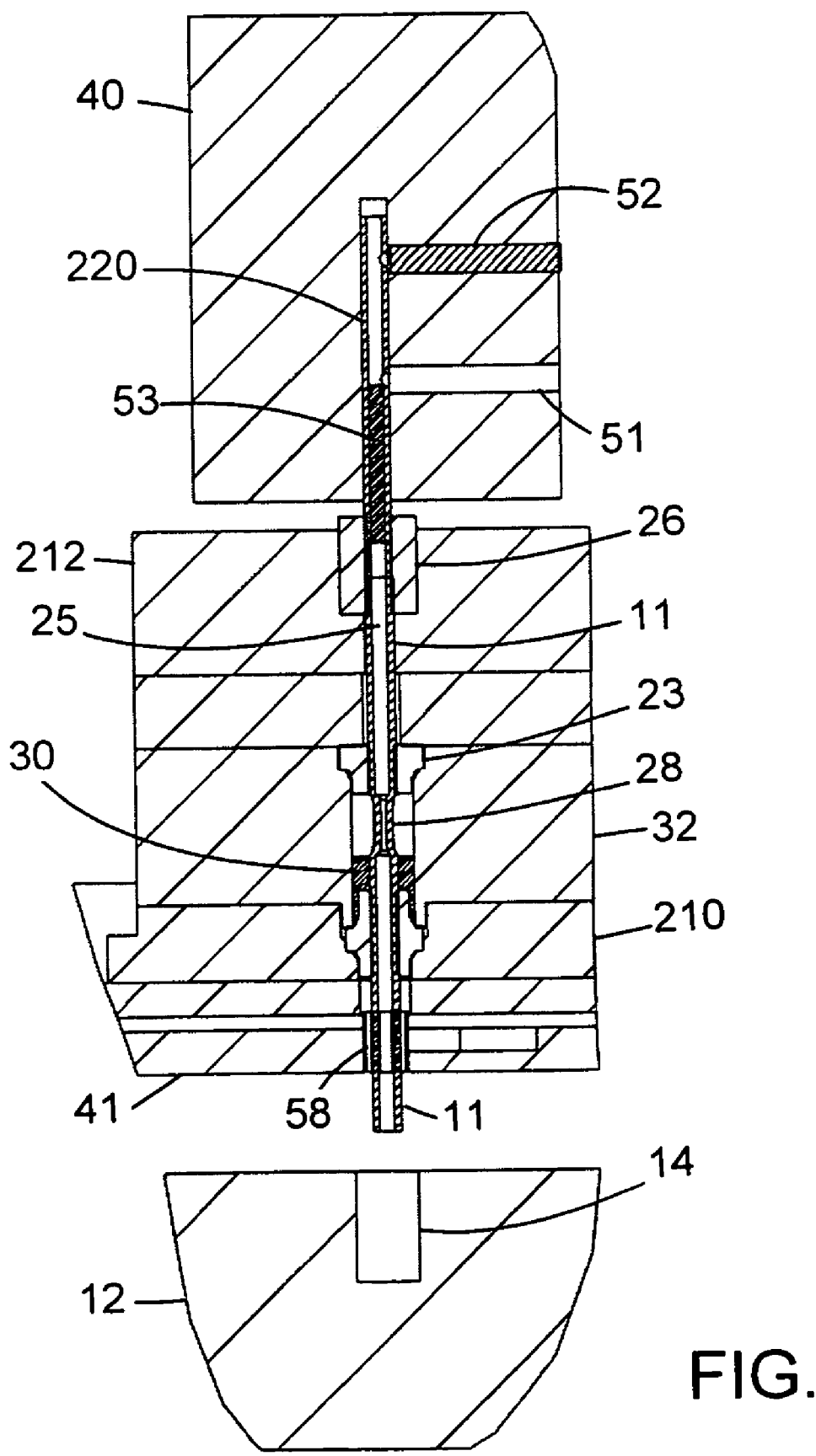
Figure 10:
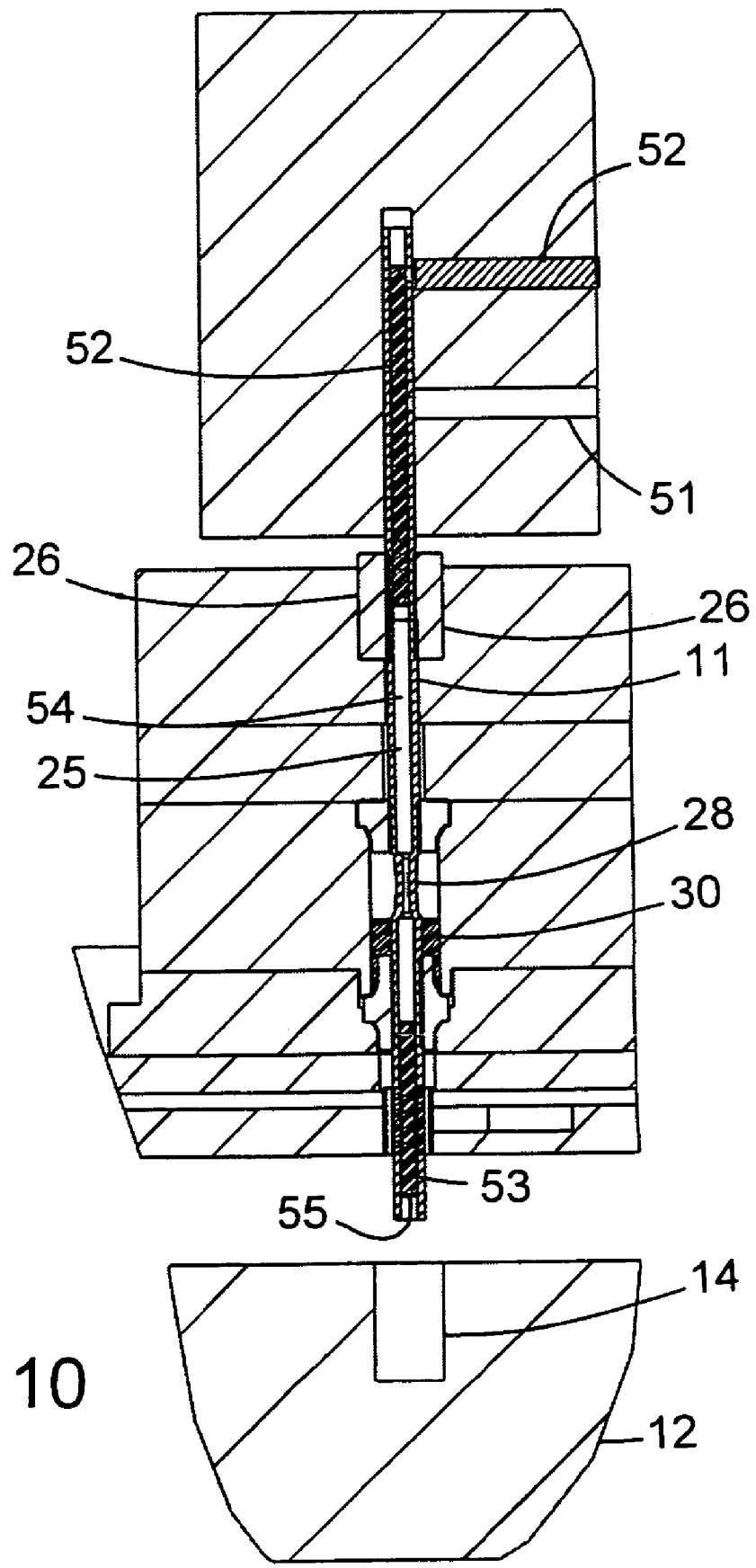

FIGS. 6 through 13 illustrate mixing and dispensing metered sample fluid with a diluent. Referring first to FIG. 6, actuation instrumentation injection block 40 is connected to devices 20 through their mechanical interfaces 26. Injection block 40 includes means for introducing a known volume of a diluent into each tube 11 and driving the diluent up and down within the tube to engage and mix with the metered sample, as discussed below. Devices 20 have also been connected to an actuation instrumentation manifold block 40 at an opposite end of tubes 11. A receptacle device 12 is disposed underneath the devices 20 such that each tube 11 is aligned with a corresponding receptacle well 14, with the capillaries 27 of the tubes each already containing a metered dose 31 of fluid sample. As seen in the side view of FIG. 7, injection block 40 defines both a driving fluid port 50 and a diluent fluid port 51 for each tap unit 20, hydraulically connected to the bore 25 of tube 11 by an injection sleeve 220 coupled to the upper end of tube 11 at interface 26 to form an air-tight seal. Driving fluid 52 and a discrete plug 53 of diluent fluid of known volume are pumped through injection block 40 to their respective entrances of sleeve 220 (FIG. 8) and then diluent fluid plug 53 is pumped into sleeve 220 (FIG. 9), such as by pneumatic operation. Driving fluid 52 is then forced into sleeve 220 (FIG. 10), hydraulically translating diluent fluid plug 53 down through mixing orifice 204 until the bottom edge or meniscus 55 of diluent fluid 53 is below meter capillary 27. Driving fluid 52 is either air, or is separated from diluent fluid 53 by air gap 54, such that the driving fluid 52 never comes in contact with the diluent plug 53. In the condition illustrated in FIG. 10, diluent plug 53 is in direct fluidic contact with the metered dose 31 of fluid sample contained within the meter capillary 27 (FIG. 6). In an amount of time typically less than about 120 seconds, meter capillary fluid sample 31 diffuses into diluent fluid 53, and may collect at the bottom meniscus 55 of the diluent fluid plug.

Figure 11:
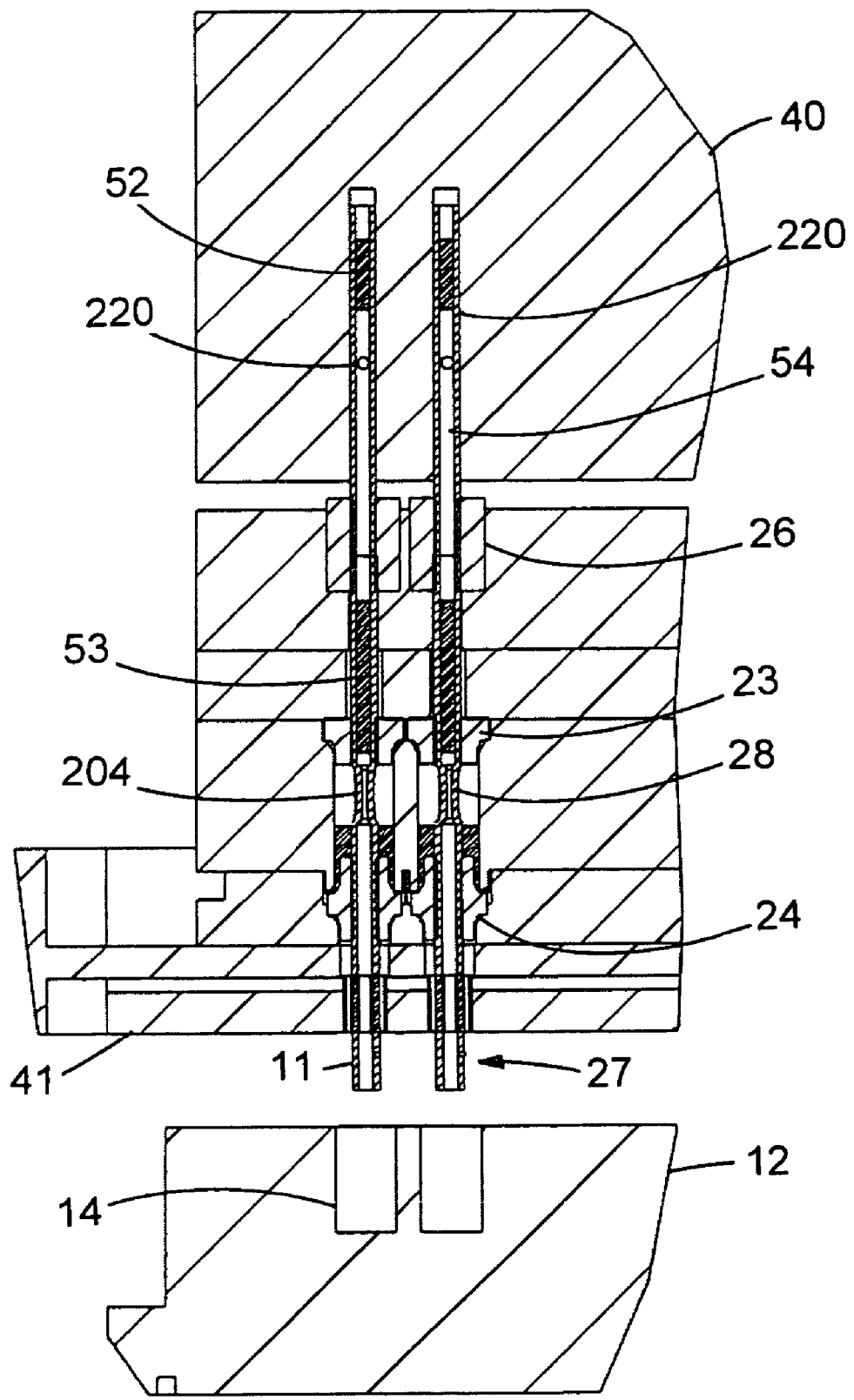
FIGS. 11-13 sequentially illustrate mixing the diluent and sample, and dispensing the solution into an assay receptacle.
Figure 12:
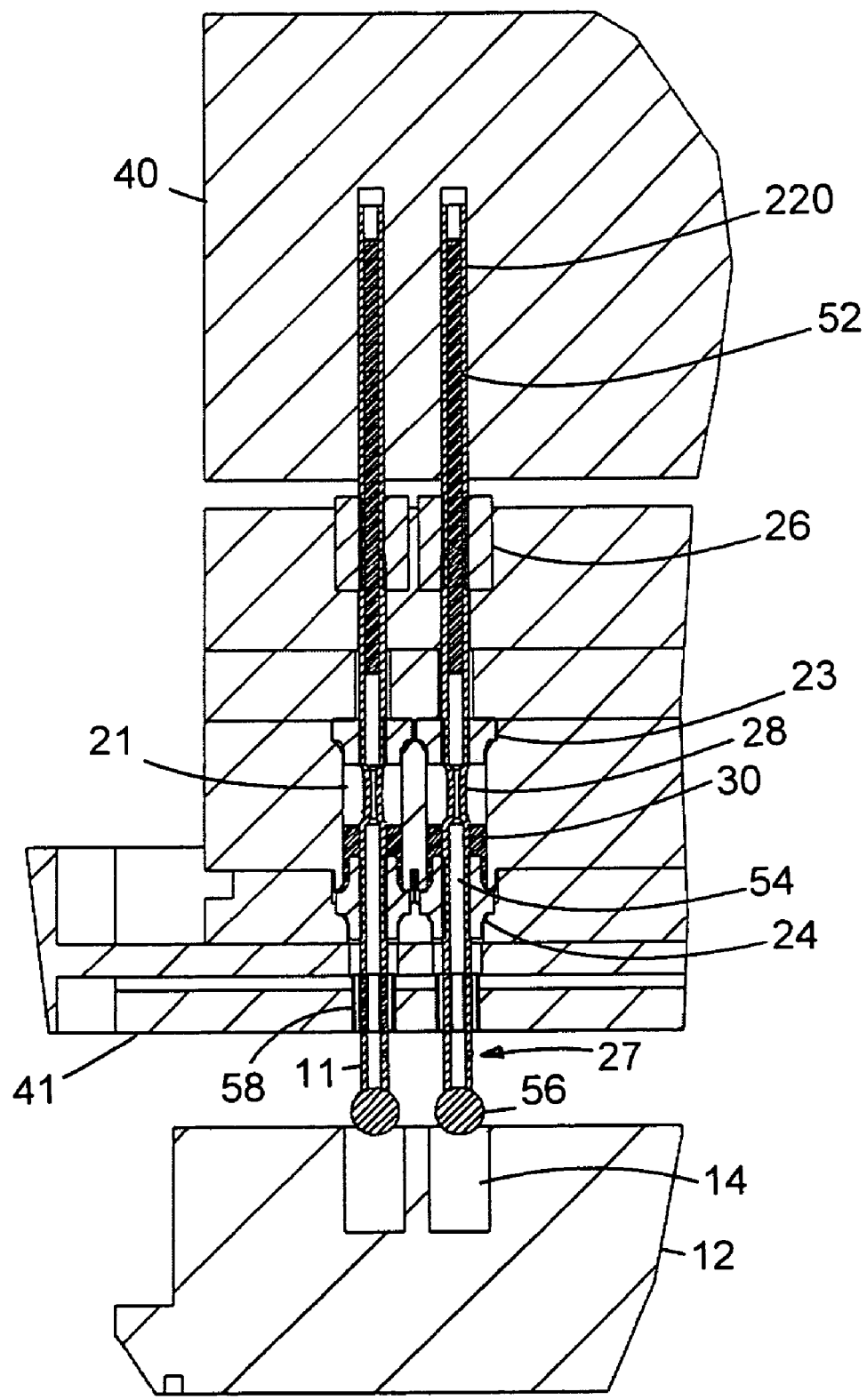
Figure 13:
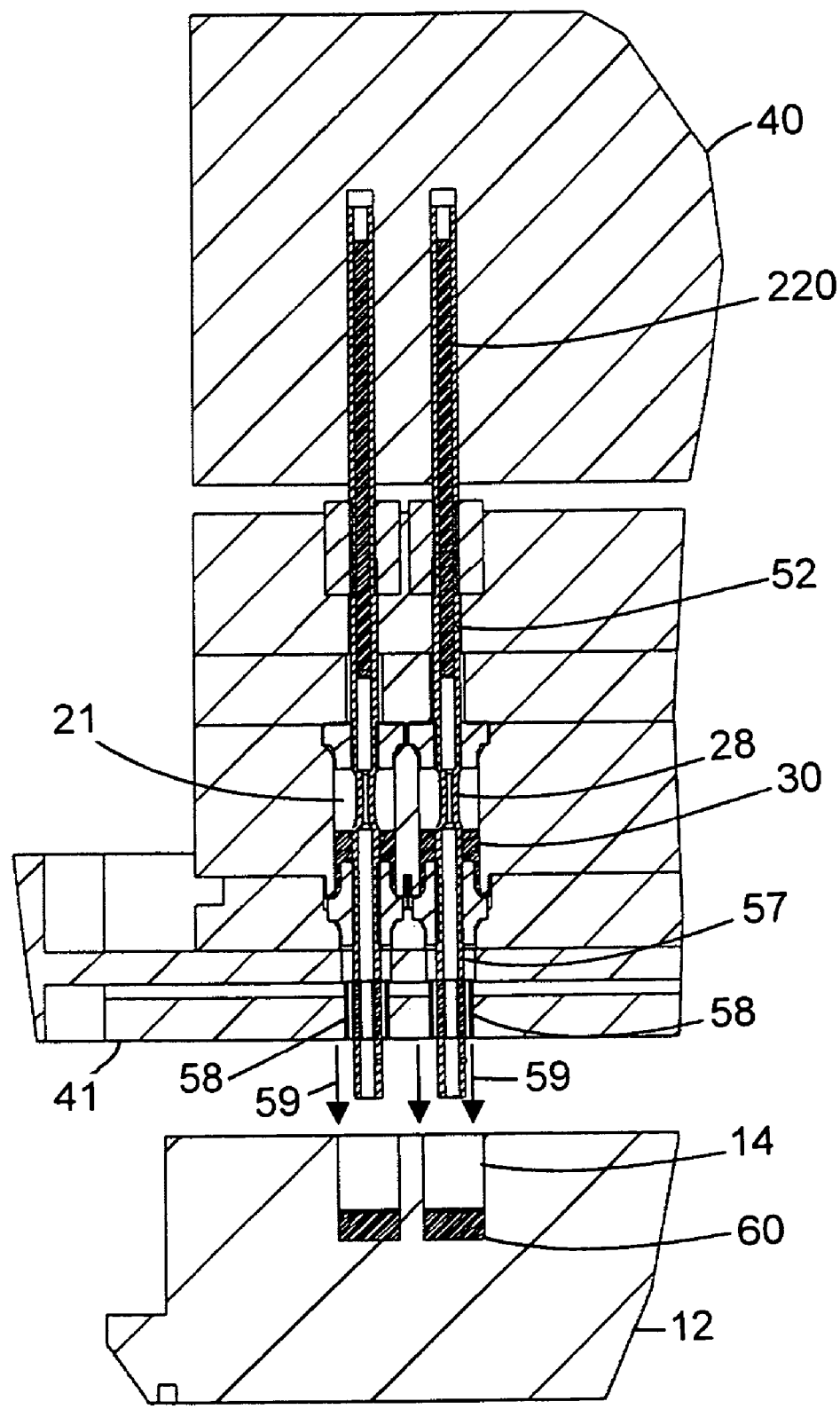

Referring next to FIG. 11, driving fluid 52 is cycled into and out of injector sleeves 220 to hydraulically translate the diluent fluid plugs 53 (now containing both the diluent and the metered doses of fluid sample drawn from capillaries 27) up and down a predetermined number of times within the bores 25 of tubes 11, through mixing orifices 204, until the solution is sufficiently mixed. The driving fluid 52 is then advanced to hydraulically translate the mixed solution plugs 53 to the bottom of tube bores 25 until proud droplets 56 of mixed solution 53 appear outside of the open ends of tubes 11 (FIG. 12). Compressed dispensing gas is then delivered through port 57 of actuation instrumentation manifold block 41, between extrusion director sleeves 58 and the outer surfaces of tubes 11 along coaxial flow paths 59, to engage the exposed surfaces of proud drops 56. The dispensing gas breaks the liquid-solid attraction between the solution droplets and their metering tubes 11, overcoming surface tension effects to enable the droplet to fall free of the tube end. Flow paths 59 need not be coaxial with tubes 11 in all cases. The gas flow pushes the proud drop 56 off of the tube 11 and into the bottom of the receptacle well 14 (FIG. 13). The dispensed solution 60 wets the bottom of the receptacle well 14. The tubes 11 of the device may now be cleaned and dried for further use.

Figure 14:
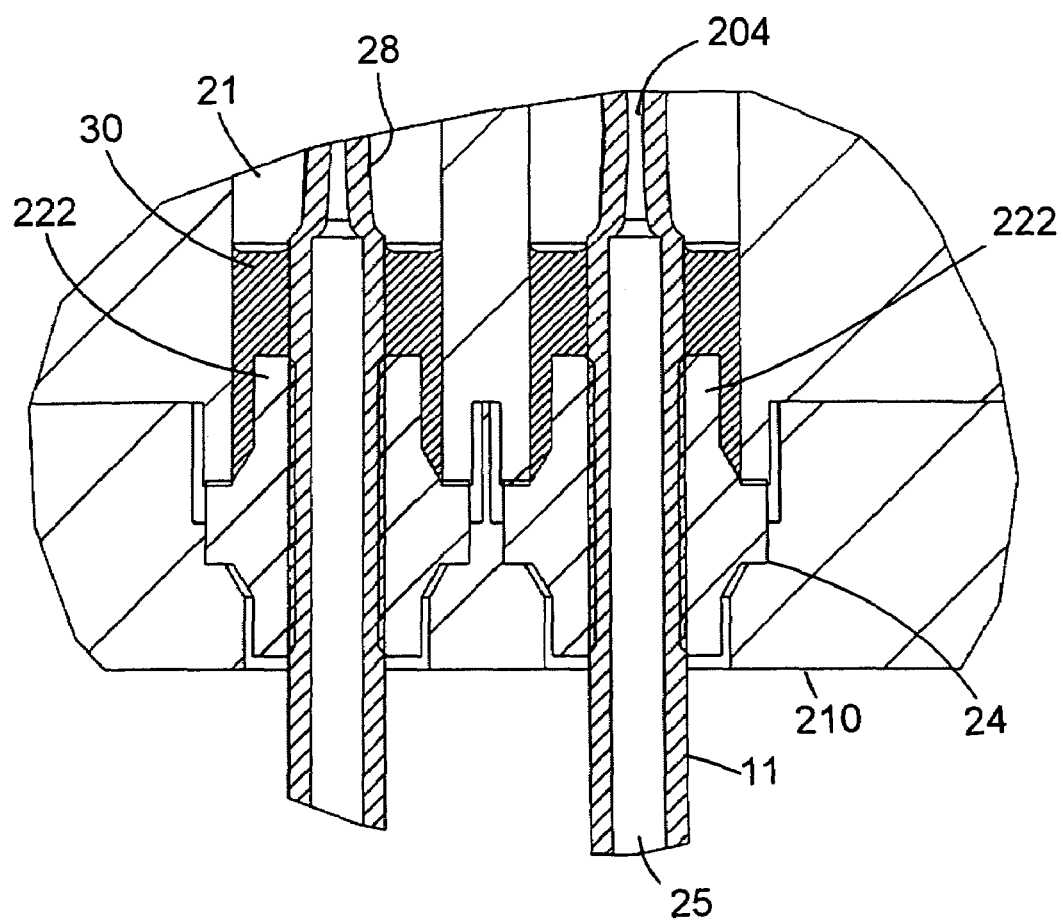
FIG. 14 is an enlarged view of the lower seal detail of FIG. 2.

Referring to FIG. 14, lower seals 24 forms a fluid-tight seal with reservoir plate 32 and tubes 11. Seals 24 each have thin cylindrical protrusions 222 of about 0.6 millimeter thickness that extend up and down the tube surface to help maintain a reliable seal against the tube surface under positive and negative pressure differentials between the reservoirs 21 and the outside environment. Alternatively, seals 24 may be molded without such protrusions 222, or with the protrusions on either top or bottom in tight engagement with seal plate 210, rather than spaced apart. Seals 24 are molded of silicone having a hardness of between about 30 and 90 shore A, coated with a layer of PTFE. The sealing bore diameter of each seal should be selected to provide a good seal against the tube surface. Seals with higher durometers can be fashioned to provide less interference against the tube, but softer seals need a tight fit to prevent losing metered fluid as the capillary is forced along the seal.

Figure 15:
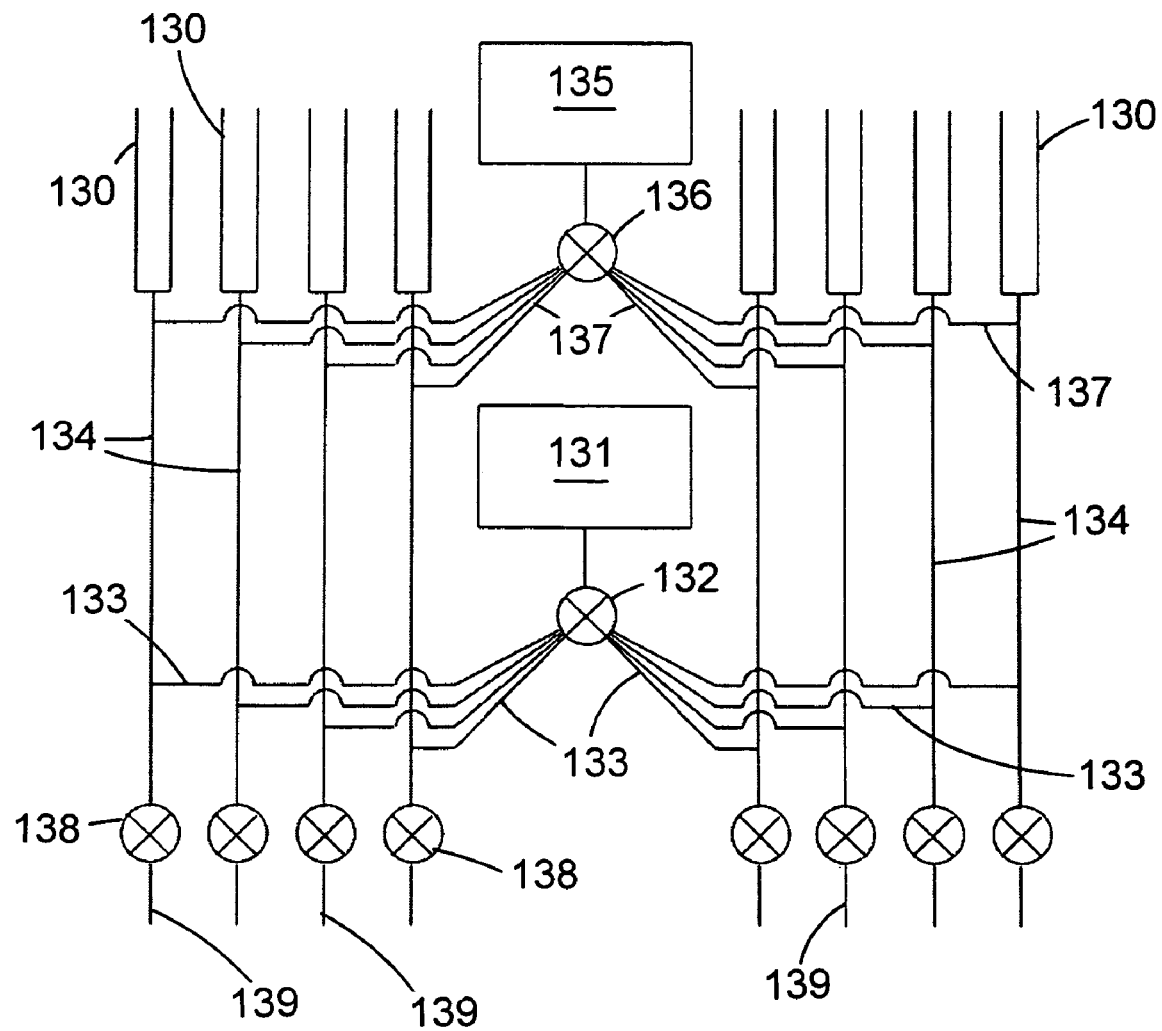
FIG. 15 schematically illustrates a system for delivering diluent to multiple tap units.

FIG. 15 shows a schematic of an eight channel injection manifold for controlling the injection of both diluent and cleaning fluid into multiple tap units along a common injection line 139 for each tap unit. Each line 139 is hydraulically connected to the tube bore 25 (FIG. 2) of a respective tap unit. A standard 96 or 384 pipette system with standard or custom tips is indicated by 130. Prior to use, diluent fluid lines 133 are purged of air for proper channel operation. The injection sequence begins when parallel or serial pinch valves 138 are closed and diluent fluid valve 132 opens and pipette 130 draws diluent fluid from diluent fluid reservoir 131 through diluent fluid valve 132, through diluent fluid lines 133 into tap unit drive lines 134. Diluent fluid valve 132 is then closed followed by parallel or serial pinch valves 138 opening. Pipette 130 pushes the diluent fluid along drive lines 134 until the diluent fluid plugs pass through parallel or serial pinch valves 138 and connecting lines 139 to be mixed with fluid sample in each tap unit.

The diluent fluid reservoir 131 is positioned such that the upper surface of the fluid is at nearly the same height as the manifold. This positioning prevents the entry of either too much fluid or not enough fluid air into the diluent fluid lines 133 due to the compressible nature of air. The predictability and accuracy of fluid control is thereby maintained.

The valves 132, 136, 138 preferably include elastomeric elements made of silicone rubber or similar elastomers. During aspiration by the pipettes 130, i.e. when the pipettes draw fluid from diluent fluid reservoir 131 into diluent fluid line 133, a control vacuum deflects elastomeric elements in the diluent and cleaning fluid valves 132, 136 away from the individual channel input ports to allow fluid flow into the tap unit drive lines 134. In the diluent fluid valve 132, a control pressure forces an elastomeric element onto each seat of the individual channel input port, thereby providing a seal. In the parallel or serial pinch valves 138, tubes are either pinched so that each channel is closed, or not pinched so that each channel is open.

To clean the tap unit drive lines 134, the main connection lines 139, and the individual tap unit lines, cleaning fluid valve 136 is opened. Cleaning fluid (i.e. solvent, air) is pumped from cleaning fluid reservoir 135 through cleaning fluid valve 136, through cleaning fluid lines 137, and into tap unit drive lines 134. The cleaning fluid then passes through connecting lines 139 into each tap unit to be expelled into a receptacle device (not shown).

Figure 16:
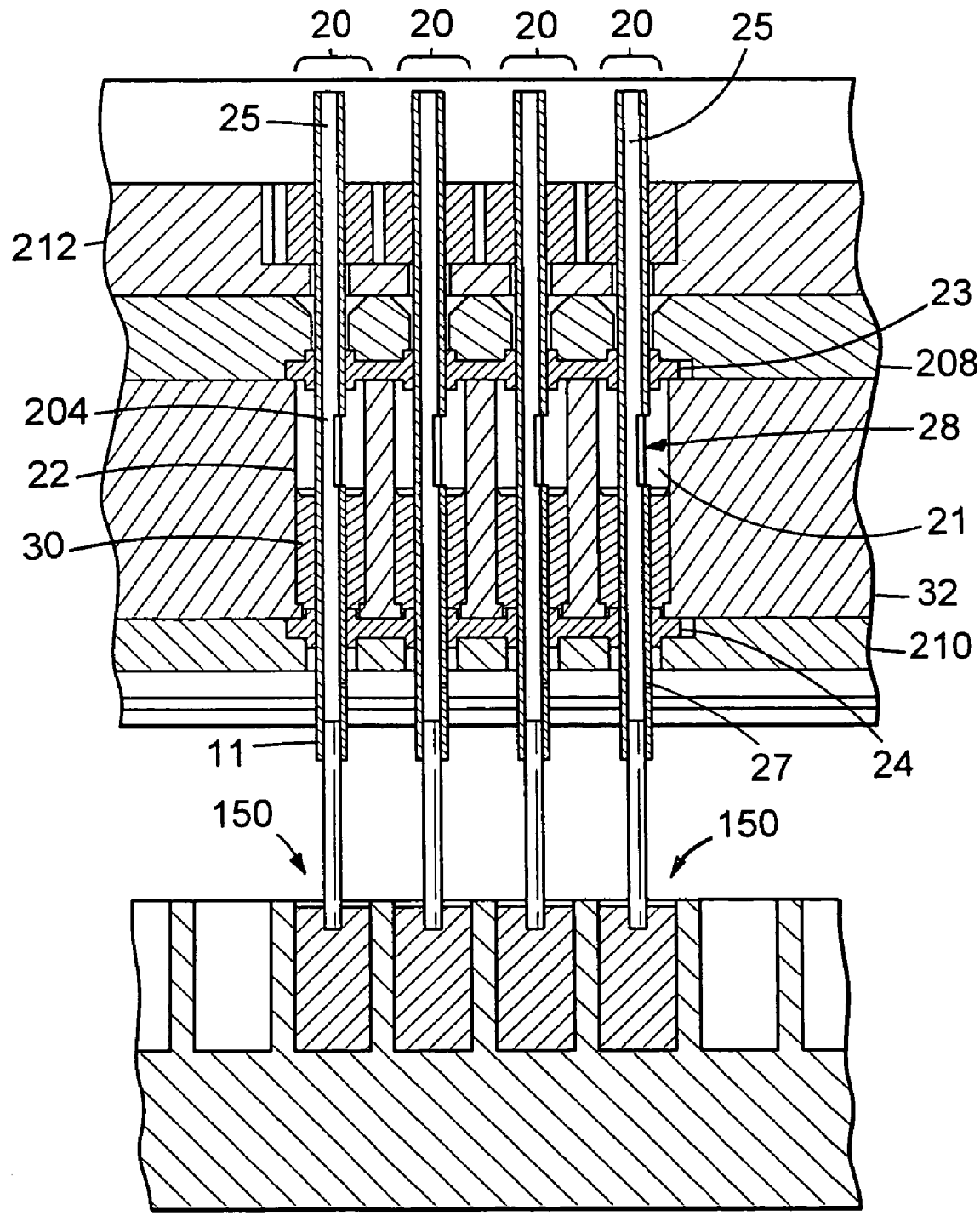
FIGS. 16 and 17 illustrate an alternative embodiment in which diluent is aspirated from a reservoir located below the tap units.
Figure 17:
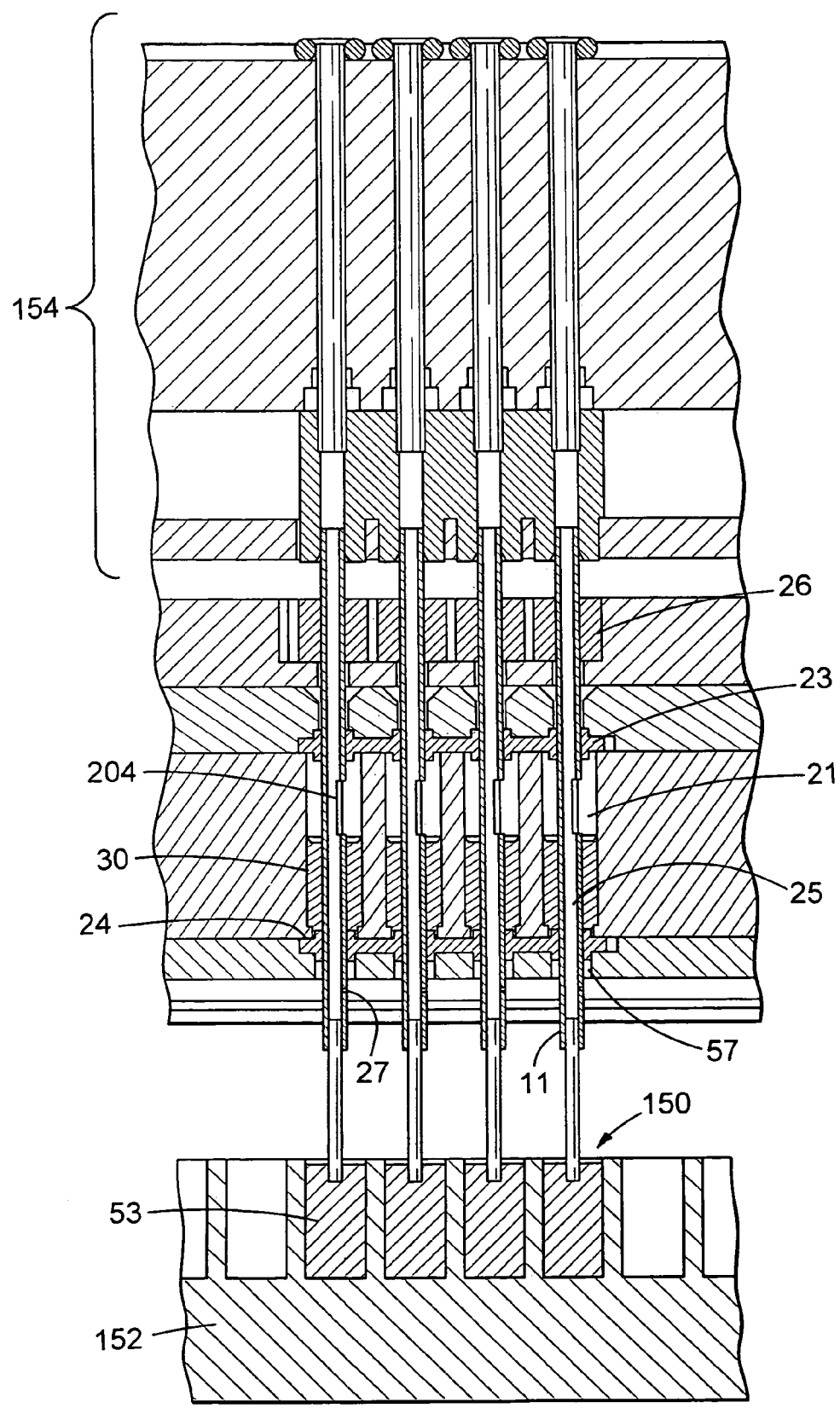

FIGS. 16 and 17 illustrate an alternative embodiment in which diluent 53 is aspirated from a diluent reservoir 150 defined in a diluent reservoir plate 152 located below the device. Fluid sample metering is identical to that disclosed above with respect to FIGS. 2-5. In this embodiment, a mechanical interface block 154 is first attached to a standard pipettor (e.g., pipettor 130 of FIG. 15) or other aspirating piece of equipment as known in the art. The pipettor mates to the liquid dispensing device 20 through mechanical interface block 154. A burst of compressed dispensing gas delivered through port 57 blows the metered dose into the center bore 25 of tube 11.

A diluent reservoir plate 152 is disposed underneath the devices 20 such that each tube 11 is aligned with a corresponding diluent reservoir well 150, with the metering capillaries 27 of the tubes already emptied of their respective metered doses of fluid sample. In this embodiment, the pipettor driving fluid is air. As the driving fluid is drawn upward by the pipettor, a slug of diluent will be aspirated into the center bore 25 of tubes 11 where it engages and mixes with sample previously blown into the bore of the tube from the metering capillary. The amount of diluent aspirated is typically between about 0 and 10 microliters.

The driving fluid is cycled up and down a predetermined number of times within the bores 25 of tubes 11, drawing the mixture of diluent and sample through mixing orifices 204, until the solution is thoroughly mixed. The driving fluid is then advanced to hydraulically translate the mixed solution plugs to thhe bottom of the tube bores 25 until proud droplets of mixed solution appear outside of the open ends of tubes 11 (see also FIG. 12).

Devices desribed herein can be designed for compatibility with various liquids, including aqueous buffers, organic solvents such as DMSO, acids, bases, proteins, oligonucleitides and reagents. Compatibility is achieved by selection of suitable materials for fabrication of components that contact the liquid. Exemplary materials for fabrication of components are stainless steel, nylon, polyethylene, polypropylene, EPD rubber, silicone rubber and PTFE. Suitable materials and fabrication of components is within ordinary skill in art.

The illustrated embodiments and the features described above build upon our prior work as disclosed in U.S. patent application Ser. No. 09/591,807, filed Jun. 12, 2000, and our corresponding PCT application US01/06174. The entire contents of both of these applications are incorporated herein by reference.

A number of embodiments of the invention have been described. Nevertheless, it will be understood that various modifications may be without departing from the spirit and scope of the invention. Accordingly, other embodiments are within the scope of the following claims.

What is claimed is:

1. A device for storing and dispensing a mixture of a first liquid and a second liquid into an array of wells in a multiwell container, the device comprising
   an array of isolated, sealed, tapped reservoir units, each unit containing an integrated metering tap including a dispensing tube having an outer surface and defining an inner cavity open at a lower end of the tube, the tube also defining a metering capillary extending through a side wall of the tube between the inner cavity and the outer surface, the metering capillary sized to draw in a known volume of the first liquid; and
   a tap drive channel in communication with the inner cavity, the tap drive channel pressurizable to
      pump the second liquid along the inner cavity of the tube so that a lower meniscus edge of the second liquid is below the metering capillary;
      draw the first liquid from the metering capillary into the second liquid via diffusion or forced vacuum;
      mix the first liquid and second liquid in the tube by hydraulically moving the second liquid up and down inside the tube, to form a mixture; and then to
      expel the mixture from the tube by pumping the mixture to the end of the tube.

2. The device of claim 1 wherein the metering capillary has a fixed volume of less than about 20 microliters, preferably between about 5 and 200 nanoliters.

3. The device of claim 1 wherein the array of reservoir units is arranged so that each tap aligns with one well of a multiwell container such as a 96-well microtiter plate, a 384-well microtiter plate, a 1536-well microtiter plate or a flat plate designed to hold small amounts of fluid.

4. The device of claim 1, further comprising:
   a reservoir housing defining, together with the outer surface of the tube, a reservoir cavity for holding a quantity of the first liquid; and
   a seal between the reservoir housing and the outer surface of the tube at a lower end of the reservoir cavity, the tube being movable against the seal between a first position, in which the metering aperture is disposed below the seal, and a second position, in which the metering aperture is disposed above the seal and exposed to the reservoir cavity for entraining a discrete dose of the first liquid within the aperture.

5. The device of claim 4 wherein the reservoir cavity is sealed against air and light.

6. The device of claim 1 wherein the inner cavity defined by the dispensing tube comprises a mixing orifice.

7. The device of claim 6 wherein the mixing orifice comprises a section of the inner cavity with a reduced diameter relative to adjacent portions of the inner cavity.

8. The device of claim 1 further comprising means for propelling the mixed solution from the tube utilizing a compressed gas, such as air, nitrogen or argon, that engages an exposed surface of the solution.

9. The device of claim 8 wherein the means for propelling the mixed solution from the tube comprises a compressed gas inlet port in fluid communication with inner cavity of the tube when the tube is in a dispense position.

10. The device of claim 8 wherein the means for propelling the mixed solution from the tube comprises a compressed gas path terminating in an annular opening surrounding the lower end of the tube.

11. A method of mixing and dispensing microliter volumes of a first liquid with a second liquid, the method including
   providing an array of isolated, sealed, tapped reservoir units, each unit containing an integrated metering tap including a dispensing tube having an outer surface and defining an inner cavity open at a lower end of the tube, the tube also defining a metering capillary extending through a side wall of the tube between the inner cavity and the outer surface, the metering cavity sized to draw in a known volume of the first liquid;
   drawing the known volume of the first liquid into the metering capillary by capillary action;
   pumping a volume of the second liquid along the inner cavity of the tube so that a lower meniscus edge of the second liquid is below the metering capillary by pressurizing a tap drive channel in communication with the inner cavity;
   drawing the dose of first liquid from the metering capillary into the second liquid via diffusion or forced vacuum;
   mixing the the first liquid and second liquid in the tube, to form a mixture by hydraulically moving the second liquid up and down inside the tube; and then
   expelling the mixture from the tube by pumping the mixture to the end of the tube.

12. The method of claim 11 wherein the volume of the second liquid is introduced into the inner cavity of the tube by injecting the second liquid into the tube at a point where the metering aperture is between the injected second liquid and said end of the tube.

13. The method of claim 11 wherein the second liquid is introduced into the inner cavity of the tube by being drawn up from the end of the tube toward the metering aperture.

14. The method of claim 11 wherein mixing includes cycling the first liquid and second liquid through a mixing orifice.

15. The method of claim 11 wherein the second liquid is moved up and down inside the tube pneumatically.

16. The method of claim 11 wherein expelling the mixture from the tube further comprises engaging an exposed surface of the mixture with a compressed gas, such as air, nitrogen or argon.

* * * * *